Figure 1:
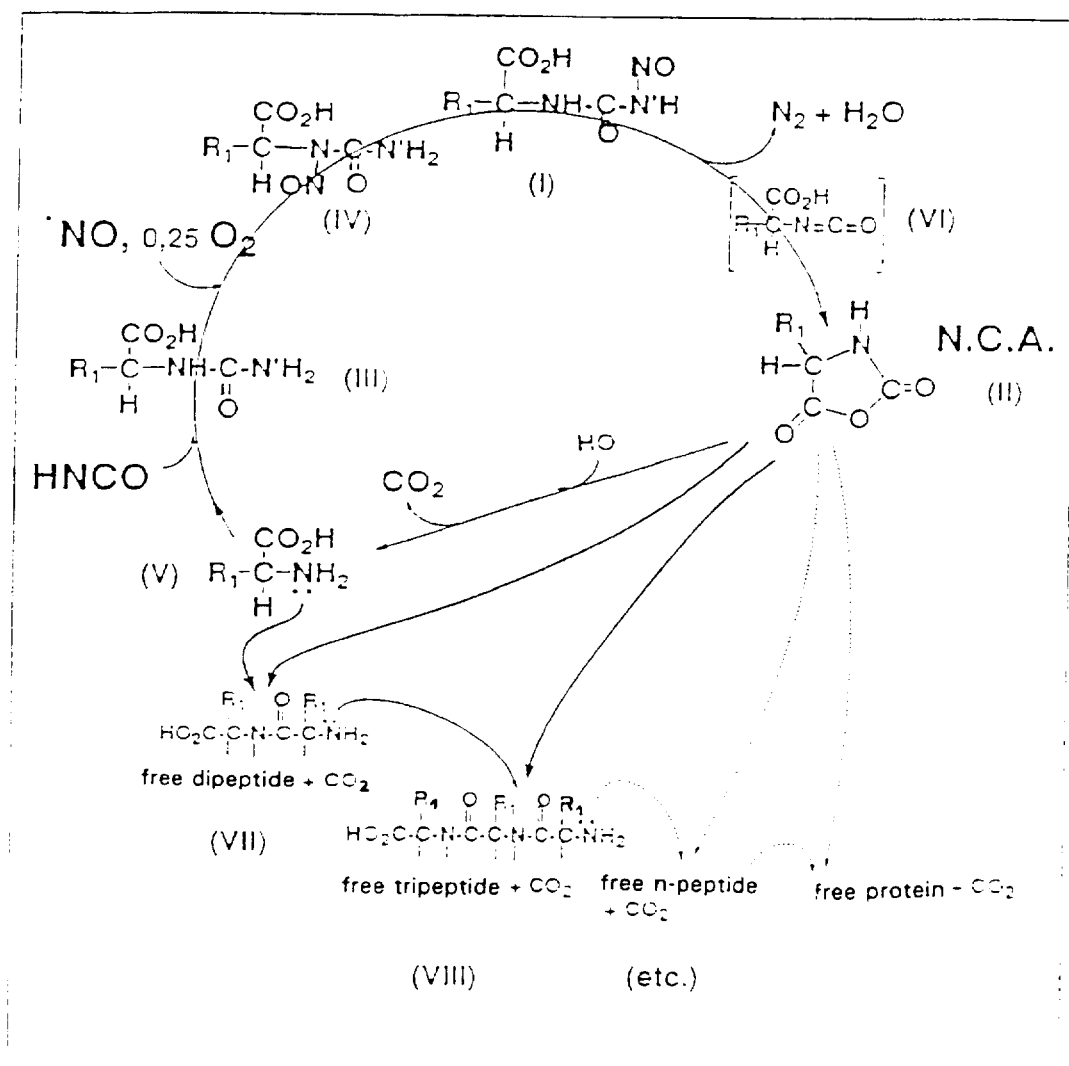

United States Patent [19]
Commeyras et al.

[11] Patent Number: 5,777,076
[45] Date of Patent: Jul. 7, 1998

[54] METHOD FOR PEPTIDE SYNTHESIS STARTING FROM N-(N'-NITROSOCARBAMOYL) AMINO ACIDS

[75] Inventors: Auguste Commeyras, Clapiers; Hélène Collet, Montpellier; Louis Mion, Montpellier; Sylvie Benefice, Montpellier; Patrick Calas, Montpellier; Henri Choukroun; Jacques Taillades, both of Clapiers; Catherine Bied, Montpellier, all of France

[73] Assignee: Universite Montpellier II Sciences et Techniques du Languedoc, Montpellier Cedex, France

[21] Appl. No.: 809,445

[22] PCT Filed: Oct. 19, 1995

[86] PCT No.: PCT/FR95/01380

§ 371 Date: May 19, 1997

§ 102(e) Date: May 19, 1997

[87] PCT Pub. No.: WO96/12729

PCT Pub. Date: May 2, 1996

[30] Foreign Application Priority Data

Oct. 24, 1994 [FR] France ............... 94 12779

[51] Int. Cl.$^6$ ............... A61K 38/00; C07K 1/00
[52] U.S. Cl. ............... 530/333; 530/338; 530/344
[58] Field of Search ............... 530/333, 338, 530/344

[56] References Cited

FOREIGN PATENT DOCUMENTS

| 0 288 795 | 11/1988 | European Pat. Off. |
|---|---|---|
| 26 15 594 | 10/1976 | Germany |
| 53-103441 | 9/1978 | Japan |
| 1 490 054 | 10/1977 | United Kingdom |

OTHER PUBLICATIONS

T. Machinami et al., "Potential Antitumor N–Carbamoyl-N'–methyl-N-'–nitroso Derivatives of Amino Acids", pp. 1333–1334, Bulletin of the Chemical Society of Japan, vol. 48, No. 4, 1975.

Wei–ci Tang et al., Synthesis of Potentially Antineoplastic Derivatives of N-|N–(2–Chloroethyl)–N–nitrosocarbamoyl| amino Acids, pp. 910–917, Arch. Pharm. (Weinheim), 314, 1981.

K. Ehresmann et al., "Syntheses of Potentially Antineoplastic Amides and Esters of N-|N'–(2–Chloroethyl)–N'–nitrosocarbamoyl| animo Acids, II$^{5)'''}$,pp. 481–487, Arch. Pharm. (Weinheim), 317, Jun. 1984.

G. Eisenbrand et al., "Synthesis and Characterization of Steroid–linked N–(2–Chloroethyl)nitrosoureas", pp. 863–872, Arch. Pharm. (Weinheim), 322, 1989.

Inouye et al J.C.S. Perkins I (1977) pp. 1905–1915.

*Primary Examiner*—Robert J. Hill, Jr.
*Assistant Examiner*—Bennett Celsa
*Attorney, Agent, or Firm*—Young & Thompson

[57] ABSTRACT

A method for peptide synthesis using an N-|N'-nitroso-(R') carbamoyl|amino acid as the starting compound. The compound is separated into $N_2$, R'OH and N-carboxyanhydride of formula (II).

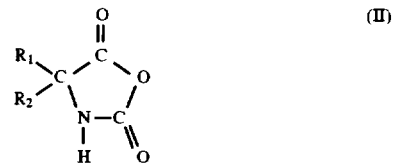

The compound (II) together with an amino acid or peptide with at least one free α-amino function is introduced into a reactive medium to obtain a dipeptide or a higher peptide than the added peptide.

11 Claims, 1 Drawing Sheet

METHOD FOR PEPTIDE SYNTHESIS STARTING FROM N-(N'-NITROSOCARBAMOYL) AMINO ACIDS

This application is a 371 of PCT/FR 95/01380 Oct. 19, 1995.

FIELD OF THE INVENTION

The invention concerns a novel method for peptide synthesis and extends to the synthesis of an intermediate N-carboxyanhydrideamino acid.

BACKGROUND OF THE INVENTION

Peptides are biologically active molecules of considerable value and their synthesis has been studied for a very long time, it being possible to carry out this synthesis by various methods, in a homogeneous phase as well as in a solid or supported phase. In either case, these methods use amino acids protected on a functional group, they create or extend the peptide on the remaining free functional group by means of a blocked amino acid, they unblock the latter functional group and they thus continue to construct the chain step by step. In order to have a free peptide, the end functional groups must obviously be unblocked. The solvent used is essentially an organic solvent. Although such methods are effective they are nevertheless very awkward.

OBJECT OF THE INVENTION

The aim of the invention is to develop a method of peptide synthesis tolerating the use of non-protected amino acids and leading directly to a free peptide.

SUMMARY OF THE INVENTION

To this end, the method according to the invention for synthesizing peptides is one wherein:

(a) an N-(N'-nitrosocarbamoyl)amino acid is prepared, having the formula:

$$\begin{array}{ccc} CO_2H & & NO \\ | & & | \\ R_1-C-N-C-N'-R' \\ | & | & \| \\ R_2 & H & O \end{array} \quad (I)$$

where $R_1$ and $R_2$ are a hydrogen or an alkyl, cycloalkyl, aryl or aryl alkyl radical, substituted or unsubstituted by one or more alcohol, thiol, amine, sulfide, acid or amide functional groups, and R' is a radical from the group: H, $CH_3$, $CH_2CH_2Cl$.

b) the compound (I) is decomposed into $N_2$, R'OH and N-carboxyanhydrideamino acid with the formula:

$$\begin{array}{c} O \\ \| \\ R_1 \diagdown \diagup C \diagdown \\ C \diagup \diagdown O \\ R_2 \diagup \diagup \diagup \\ N-C \\ | \quad \| \\ H \quad O \end{array} \quad (II)$$

c) an addition reaction is carried out between the compound (II) and an amino acid or a peptide having at least one free α-amino functional group, with a view to obtaining a dipeptide or a higher peptide than the added peptide.

The inventors have surprisingly shown that it is possible to obtain free peptides directly, i.e. having their amino functional group unprotected, by the action of N-(N'-nitrosocarbamoyl)amino acids (I) on an amino acid or a peptide having its α-amino and carboxyl function group free. The method of the invention enables a free dipeptide to be created or enables the initial peptide to be extended by one unit. The peptide bond thus formed is that linking the amine functional group of the amino acid (or of the peptide) present in the medium with the carboxyl group of the compound (I).

In the case where the carboxyl functional group of the amino acid (or of the peptide with n amino acid fragments) present in the solution or added thereto, is blocked, the dipeptide or the peptide with (n+1) amino acids formed, can retain the blocking of this functional group.

According to a preferred embodiment, a compound (I) is selected as the starting compound in which R' is a hydrogen, with a view to obtaining water as a decomposition by-product at the end of the decomposition (b). This water may remain associated with the peptide formed without inconvenience and without the necessity of separating it.

It is possible to select a natural amino acid residue as the $R_1$ radical and hydrogen as the $R_2$ radical with a view to synthesizing natural peptides. A modified amino acid residue may also be selected as the $R_1$ radical and a methyl, ethyl, propyl group as the $R_2$ radical, so as to obtain a modified peptide. As this is known per se, this modification may enable the properties of the peptides to be modified according to the applications.

The process of the invention is advantageously put into practice according to the two operating methods described below.

In the first place, the decomposition reaction (b) may be carried out in an anhydrous organic solvent. In this case, the addition reaction (c) consists of adding an amino acid or a previously prepared peptide to the reaction medium. Experiments seem to show that this operating method leads to peptides with a high molecular weight.

Another operating method consists of carrying out the decomposition (b) in an aquo-organic medium at a pH substantially between 6 and 10. The molecular weight of the peptides obtained in this case is significantly lower.

It is possible to carry out the addition by adding an amino acid or a previously prepared peptide to the aquo-organic medium. When this method is carried out in an aquo-organic medium buffered by means of an alkali metal bicarbonate (pH of between 6.5 and 7.5), a single amino acid (resulting from the decomposition) can be added to the amino acid or the peptide introduced into the medium. Such a "step-by-step" technique offers the possibility of synthesizing a desired heteropeptide by repeated syntheses.

In an aquo-organic medium, it is also possible, without introducing amino acids or peptides into the medium, to carry out an addition on the N-carboxyanhydride of an amino acid derived from partial hydrolysis of this N-carboxyanhydride. In this case a homopeptide is obtained of which the molecular weight increases as the percentage of water in the medium decreases.

The temperature conditions of the decomposition (b) and of the addition (c) do not appear to be critical and in practice it is possible to operate at room temperature. However, in certain cases, a higher temperature may be selected for the decomposition in order to encourage it (50° C. for example) whereas a lower temperature (of the order of −10° C.) reduces the risks of interfering reactions in the addition reaction.

It should be noted that the synthesis of N-(N'-nitrosocarbamoyl)amino acids (I) is described in the literature (DE-OS 2,615,594, Japan Kokai 78 103,441, EPA 88

105 584 2 for R'=H and Bul Chem Soc Japan, vol. 48 (4), 1333–1334 (1975), Arch. Pharm. Weinheim 314,910–917 (1981), 317,481–487 (1984), 322,863–872 (1989), for R'=CH$_3$, ClCH$_2$CH$_2$— etc). They are described in the case where R'=H, as decomposing in an acid medium at pH values less than 4 giving the corresponding amino acid, nitrogen and carbon dioxide (see EP-A-88 105 584 2). They have been used up to now for hydrolysing the carbamoyl functional group. The substituted derivatives (R'=CH$_3$, ClCH$_2$CH$_2$— etc) form part of the family of N'-alkylated nitroso-ureas. Their antitumoral properties have been studied, which would result from their alkylating power (Arch. Pharm. 322,863–872 (1989)).

According to one feature of the process of the invention, the compounds (I) may be synthesized directly in an anhydrous reaction medium (dioxan, acetonitrile, etc), an aqueous reaction medium at a pH of less than 4 or an aquo-organic reaction medium at a pH of less than 4 by the action of a nitrosing agent such as NO, NO$_2$H, N$_2$O$_3$, N$_2$O$_4$, etc used pure or in a mixture with an oxidising agent (oxygen, or any other agent such as Fe$^{3+}$, Cu$^{2+}$, metallic couples or electrochemical oxidation) on an N-|N'-(R')carbamoyl| amino acid having the formula

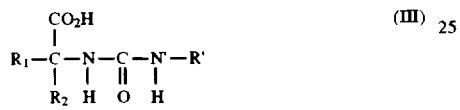

(III)

A reaction intermediate in this reaction has been determined as being the N-nitroso-N-carbamoylamino acid having the formula (IV) which, under different operating conditions from those used in this process, may partly decompose to give an α-hydroxy acid:

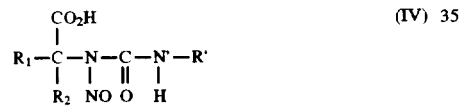

(IV)

The compounds (I) may also be prepared in situ in the reaction medium in two stages:

by first of all reacting, at a pH of less than 8, isocyanic acid (HNCO), a salt of this acid or a methyl or chloroethyl isocyanate with an amino acid to obtain an N-|N'-(R')carbamoyl|amino acid having the formula:

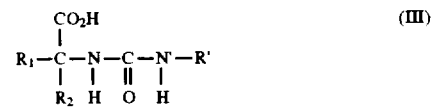

(III)

and then reacting a nitrosing agent with the N-|N'-(R') carbamoyl|amino acid formed.

It should be emphasized that the amino acids used (added compounds or starting compounds) may have a D or L chirality, or may be racemic. When the compounds used are enantiomerically pure, they do not racemize during the reaction. Peptides synthesized by using the process described above contain traces of N-[N'-(R')carbamoyl] amino acid (III) which makes it possible to know whether they were prepared by the method of the invention.

The single figure of the drawing shows the mechanism for the peptide synthesis aimed at by the invention in the particular case where R$_2$=H and R'=H. According to this mechanism, whatever its degree of substitution, the compound (I) decomposes with liberation of nitrogen and water (or alcohol according to the nature of R') giving an N-carboxyanhydride (NCA) (II), via an α-isocyanato acid (VI) according to the hypothesis formulated in the single figure. In spite of their sensitivity to hydrolysis, the (NCAs) (II) react concurrently in an aqueous medium (and of course in an anhydrous medium) with the free (namely non-protonated) amino functional groups of the amino acids (V) giving peptides (VII, VIII, etc) of which the terminal amino functional group spontaneously loses carbon dioxide.

The invention extends to the synthesis of the intermediate compound N-carboxyanhydrideamino acid (II), obtained by decomposing an N-(N'-nitrosocarbamoyl)amino acid (I).

When this decomposition is carried out in an anhydrous organic solvent, an N-carboxyanhydrideamino acid is recovered having greater thermal stability, after evolution of nitrogen and separation of the organic solvent containing the water formed (these operating conditions prevent hydrolysis of the compound (II)).

The method of the invention is illustrated hereinafter by means of practical examples.

EXAMPLE 1

Synthesis of N-(N'-nitrosocarbamoyl)valine
(compound I in which R$_1$=iPr, R$_2$=H, R'=H)
starting from N-carbamoylvaline (compound III with the aforementioned radicals).

1 mmole (160 mg) of racemic N-carbamoylvaline was placed with stirring in 20 ml of anhydrous dioxan at 20° C. The solution was purged for ½ hour with a current of nitrogen. A gaseous mixture of 66 ml of NO and 25 ml of air (70% NO) was then added to this solution. After ¼ hour of reaction, the solvent and the excess nitrosing agent were driven off under reduced pressure giving a colourless mass (190 mg) which crystallized. The solution was analysed by HPLC (high pressure liquid chromatography), on a C$_{18}$ column with a 9/1 water/acetonitrile solution as eluent containing 0.05% CF$_3$COOH and detected in UV at 220 nm. Isocratic analysis at 1 ml/min gave two signals at 22 and 28 min with a relative intensity of 30/70. A new analysis of the same reaction medium 60 minutes after the preceding one showed that the relative intensity of these two signals was inverted to 70/30. Analysis by NMR $^1$H (nuclear magnetic resonance of the proton) of these two situations enabled it to be established that the products corresponding to these two signals were respectively, N-(N'-nitrosocarbamoyl)valine (I) NMR $^1$H (DMSO-d6+TMS); δ (ppm): 0.85 (d, 3H, CH$_3$); 0.95 (d, 3H, CH$_3$); 2.1 (m, 1H, CH); 4.3 (dd, 1H, CH); 7.3 (s, 1H, NH); 9.15 (s, 1H, NH) and N-nitroso-N-carbamoylvaline (IV) NMR $^1$H, (DMSO-d6+TMS) ; δ (ppm): 0.85 (d, 3H, CH$_3$); 0.95 (d, 3H, CH$_3$); 2.1 (m, 1H, CH); 4.3 (dd, 1H, CH); 9.0 (s, 2H, NH$_2$).

A third analysis 60 minutes after the preceding one showed the disappearance of the signal at 28 min in favour of the signal 22 min thus corresponding to the virtually quantitative formation of N-(N'-nitrosocarbamoyl)valine (I) even though in the latter chromatogram a signal at 17 min started to appear with a very low intensity which was analysed in example 2 below.

EXAMPLE 2

Synthesis of N-carboxyanhydridevaline (II; R1=iPr, R2=H) starting from N-(N'nitrosocarbamoyl)valine (I)

1 mmole of N-(N'nitrosocarbamoyl)valine (I) resulting from the preceding example, placed in 20 ml of anhydrous dioxan under an atmosphere of helium, was held at 30° C for 30 minutes during which evolution of gas was observed within the solution. This evolution was analysed by mass spectroscopy as being molecular nitrogen (mass 28). Analysis of the solution by HPLC then showed the presence of a single signal at 17 min and the disappearance of the signal at 22 min. The reaction medium was then evaporated under reduced pressure so as to remove the solvent and the water formed during the reaction. The crystallized crude product (145 mg) was identified, by comparing it with an authentic example, as being N-carboxyanhydridevaline.

Melting point=75° C. for the crude product and 81° C. after recrystallization; NMR $^1$H (DMSO-d6+TMS); δ (ppm): 0.25 (d, 3H, $CH_3$); 0.95 (d, 3H, $CH_3$); 2.1 (m, 1H, CH); 9.15 (S, 1H, NH).

EXAMPLE 3

Synthesis of N-carboxyanhydridevaline (II; R1=iPr, R2=H) starting from N-carbamoylvaline (III) in an organic solvent.

1 mmole of N-carbamoylvaline was placed in 20 ml of acetonitrile (containing less than 0.1% of water) at room temperature and in an atmosphere of nitrogen. The nitrosing mixture (66 ml NO+26 ml air) was added. After 30 minutes of reaction, the excess nitrosing agent and the solvent were driven off under reduced pressure. Analysis of the solution of the crude crystallized product (MPt 74° C.) by HPLC showed the presence of a single signal at 17 min characteristic of N-carboxyanhydridevaline. Its NMR spectrum was in agreement with that given in example 2.

EXAMPLE 4

Synthesis of N-carboxyanhydridevaline (II; R1=iPr, R2=H) starting from N-carbamoylvaline (III) in an aquo-organic medium.

1 mmole of N-carbamoylvaline was placed in 20 ml of water at room temperature under an atmosphere of nitrogen. The nitrosing mixture (264 ml of NO+104 ml of air) was added.

After 30 minutes of reaction, the excess nitrosing agent and the solvent were driven off under reduced pressure. Analysis of the solution of the crude product by HPLC showed the presence of the signal at 17 min characteristic of N-carboxyanhydridevaline as well as the signal at 4.8 min of valine in the ratio 80/20.

EXAMPLE 5

Synthesis of N-carboxyanhydridevaline (II; R1=iPr, R2=H) starting from valine (V) in an aquo-organic medium.

1 mmole of valine and 3 mmole of potassium cyanate were added to 20 ml of water at room temperature (pH equal to 4). The formation of N-carbamoylvaline (III) was followed by HPLC. When the formation of N-carbamoylvaline (III) was complete (at the end of 2 hours) the medium was placed under an atmosphere of nitrogen and the nitrosing mixture (264 ml of NO+104 ml of air) was added. After 30 min of reaction, the excess nitrosing agent and the solvent were driven off under reduced pressure. HPLC analysis showed, as in example 4, the presence of a characteristic signal of N-carboxyanhydridevaline as well as a lower intensity signal of valine in the ratio 80/20.

EXAMPLE 6

Synthesis of the Val—Val dipeptide starting from N-carboxyanhydridevaline (II).

1 mmole of D,L-N-carboxyanhydridevaline (II), prepared as in example 2 or 3, was placed in 5 ml of acetonitrile. An aquo-organic solution (10 ml $H_2O$+8 ml $CH_3CN$) containing 1 mmole of the sodium salt of D,L-valine and 2 mmoles of $Na_2CO_3$ was then added at −10° C. (pH=7).

After 30 minutes of reaction at −10° C., the reaction mixture was acidified and the solution was analysed by HPLC, the free Val—Val dipeptide being characterized by comparison with an authentic sample (HPLC 6.97 min). The crude product obtained was recrystallized and identified by its mass spectrum M+1=217. The yield was 95%.

EXAMPLE 7

Synthesis of the Val—Val dipeptide starting from D,L-N-(N'-nitrosocarbamoyl)valine (I).

1 mmole of D,L-N-(N'-nitrosocarbamoyl)valine (I), prepared as in example 1, was placed in 5 ml of acetonitrile at 30° C. for 60 min. An aquo-organic solution (10 ml of $H_2O$+8 ml of $CH_3CN$) containing 1 mmole of the sodium salt of D,L-valine and 2 mmoles of $Na_2CO_3$ were then added at −10° C. (pH=7).

The remainder of the reaction was identical to example 6.

EXAMPLE 8

Synthesis of the Val-Ala-Phe tripeptide starting from N-(N'-nitrosocarbamoyl)valine.

According to the same procedure as in example 7, 1 mmole of the sodium salt of the Ala-Phe dipeptide was added to the solution of N-(N'-nitrosocarbamoyl)valine.

The Val-Ala-Phe tripeptide was obtained and identified from an authentic sample by HPLC and mass spectroscopy. The yield of the crystallized product was 80 W.

EXAMPLE 9

Synthesis of the Ala-Phe dipeptide starting from N-|N'-nitroso-N'-(2-chloroethyl)carbamoyl|alanine.

According to the same procedure as in example 7, 1 mmole of the sodium salt of phenylalanine was added to a solution of N-|N', N'-(2-chloroethyl)nitrosocarbamoyl| alanine (NMR $^1$H (DMSO-d6+TMS);δ (ppm): 1.4 (d, 3H, $CH_3$); 3.6 (t, 2H, $CH_2$); 4.1 (t, 2H, $CH_2$); 4.4 (q, 1H, CH); 8.9 (d, 1H, NH).

The Ala-Phe dipeptide was obtained and identified from an authentic sample by HPLC and mass spectroscopy. Yield: 40%.

EXAMPLE 10

Synthesis of N-(N'-nitrosocarbamoyl)alanine (I; $R_1=CH_3$, $R_2=H$, R'=H) followed by its decomposition into N-carboxyanhydridealanine (II).

1 mmole (132 mg) of D,L-N-carbamoylalanine (III) was reacted as in example 1. HPLC analysis (eluent: water/acetonitrile 95/5+0.05% $CF_3CO_2H$) showed, as for valine, the formation of a species under kinetic control at 15 min then changing into another species characterized by a signal at 11 min. The NMR $^1$H spectrum (DMSO-d6+TMS); δ (ppm): 1.2 (d, 3H, $CH_3$); 4.05 (q, H, CH); 8 (s, 1H, NH) 8.95 (s, 1H, NH) characterized the N-(N'-nitrosocarbamoyl) alanine. The latter species changed in its turn to give quantitatively D,L-N-carboxyanhydridealanine characterized by its HPLC retention time at 6.9 min, its melting point (60° C.) and its NMR spectrum.

EXAMPLE 11

Synthesis of D,L-N-(N'-nitrosocarbamoyl) methionine (I; $R_1=CH_3S(CH_2)_2$—, $R_2=H$, R'=H) followed by its decomposition into N-carboxyanhydridemethionine (II).

1 mmole (192 mg) of N-carbamoylmethionine (III) was placed in 20 ml of acetonitrile and treated according to the procedure of example 1. After 5 minutes of reaction, the excess nitrosing agent and the solvent were removed under reduced pressure.

Analysis of the solution by HPLC showed:

- a very low intensity peak at 28 min characterizing the residual presence of N-nitroso-N-carbamoylmethionine (IV),

- a very intense peak at 22 min characterizing N-(N'-nitrosocarbamoyl)methionine: (I) {NMR $^1$H (DMSO-d6+TMS); δ (ppm): 2.02 (m, 2H, $CH_2$); 2.06 (s, 3H, $CH_3$); 2.55 (t, 2H, $CH_2$); 4.58 (t, 1H, CH); 7.9 (s, 1H, NH); 8.2 (s, 1H, NH)}.

- an equally very intense peak at 17 min characterizing N-carboxyanhydridemethionine (II) {NMR $^1$H (DMSO-d6+MS);δ (ppm): 2.02 (m, 2H, $CH_2$); 2.06 (s, 3H, $CH_3$); 2.55 (t, 2H, $CH_2$); 4.6 (t, 1H, CH); 9.1 (s, 1H, NH)}.

In the case of methionine, total decomposition of compound (I) into compound (II) required an energy input greater than in the preceding examples (50° C. for several hours).

Hydrolysis of the compound (II) obtained in this way led to 93% methionine and 7% methionine sulfoxide, showing the existence of possibilities of controlling the oxidizing power of the nitrosing agent used.

EXAMPLE 12

Analysis of traces of N-carbamoylamino acids (III) in the peptides synthesized.

The HPLC method previously used enabled the N-carbamoylamino acids (III) to be detected at concentrations as low as $10^{-1.6}$ moles per liter.

The peptides synthesized by this method showed, after crystallization, the presence of traces of N-carbamoylamino acids (III) of less than a ppm but nevertheless visible in the background noise of the chromatogram.

We claim:

1. A method for peptide synthesis, comprising preparing an N-{N'-nitroso-N'-(R') carbamoyl}amino acid having the formula:

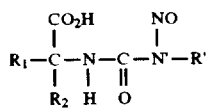

where $R_1$ and $R_2$ are a hydrogen or an alkyl, cycloalkyl, aryl or aryl alkyl radical, substituted or unsubstituted by one or more alcohol, thiol, amine, sulfide, acid or amide functional groups, and R' is a radical from the group: H, $CH_3$, $CH_2CH_2Cl$, decomposing the compound (I) into $N_2$, R'OH an and N-carboxyanhydrideamino acid having the formula:

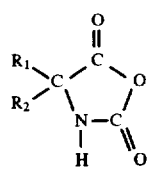

carrying out an addition reaction between the compound (II) and an amino acid or a peptide having at least one free α-amino functional group, to obtain a dipeptide or a higher peptide than the added peptide.

2. The method as claimed in claim 1, wherein (a) a compound (I) is prepared in which R' is a hydrogen, and water is obtained as a decomposition by-product at the end of the decomposition.

3. The method as claimed in claim 2, wherein a compound (I) is prepared in which $R_1$ is an amino acid residue and $R_2$ a hydrogen or a methyl, ethyl or propyl group.

4. The method as claimed in claim 1, wherein:
   the compound (I) is decomposed in an anhydrous organic solvent, and
   the addition reaction consists of adding an amino acid or a previously prepared peptide to a reaction medium.

5. The method as claimed in claim 1, wherein:
   the compound (I) is decomposed in an aqueous-organic medium at a pH substantially between 6 and 10, and
   the addition reaction consists of adding an amino acid or a previously prepared peptide to a reaction medium.

6. The method as claimed in claim 5, wherein to carry out the decomposition and the addition an aqueous-organic medium is used buffered by means of an alkali metal bicarbonate to a pH of between 6.5 and 7.5, to add a single amino acid resulting from the decomposition to the amino or a peptide introduced into the medium.

7. The method as claimed in claim 1, wherein:
   decomposition of the compound (I) is carried out in an aquo-organic medium at a pH substantially between 6 and 10, and
   the addition reaction is carried out between the compound (II) and an amino acid resulting from partial hydrolysis of the compound (II).

8. The method as claimed in claim 1, wherein N-{N-nitroso-N'-(R')carbamoyl}amino acid is synthesized directly in the reaction medium by the action of a nitrosating agent on an N-|N'-(R')carbamoyl|amino acid having the formula:

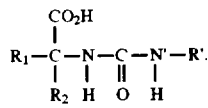

9. The method as claimed in claim 1, wherein N-|N'-nitroso-N'-(R')carbamoyl|amino acid is synthesized directly in the reaction medium in two stages:

by first reacting isocyanic acid, a salt of this acid or a methyl or chloroethyl isocyanate with an amino acid to obtain an N-|N'-(R')carbamoyl|amino acid having the formula:

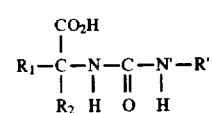

and by then reacting a nitrosating agent with the N-{N'-(R')carbamoyl}amino acid formed.

10. A process for synthesizing an intermediate compound N-carboxyanhydrideamino acid having the formula:

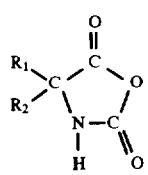

comprising decomposing an N-(N'-nitrosocarbamoyl amino acid having the formula:

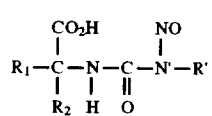 (I)
and recovering N-carboxyanhydride after evolution of nitrogen.
11. The process as claimed in claim 10, wherein decomposition of the compound (I) is carried out in an anhydrous organic solvent, and separating the solvent which contains evolved water upon recovery of the N-carboxyanhydride.
* * * * *